United States Patent [19]

Amerena

[11] Patent Number: 4,860,753

[45] Date of Patent: Aug. 29, 1989

[54] MONITORING APPARATUS

[75] Inventor: William A. Amerena, Middleton, Mass.

[73] Assignee: The Gillette Company, Boston, Mass.

[21] Appl. No.: 117,211

[22] Filed: Nov. 4, 1987

[51] Int. Cl.$^4$ .............................................. A61B 5/00
[52] U.S. Cl. ................................... 128/632; 324/61 P
[58] Field of Search .............. 128/632, 639, 734, 800, 128/801; 324/61 R, 61 P, 61 QS

[56] References Cited

U.S. PATENT DOCUMENTS

| | | | |
|---|---|---|---|
| 712,220 | 10/1902 | Vetter | 128/801 |
| 2,208,023 | 7/1940 | Ellis | 128/800 |
| 2,522,052 | 9/1950 | Logan et al. | 128/734 |
| 2,852,739 | 9/1958 | Hansen | 324/61 |
| 3,761,810 | 9/1973 | Fathauer | 324/61 R |
| 4,013,065 | 3/1977 | Copeland et al. | 128/632 |
| 4,096,852 | 6/1978 | Adams | 128/734 |
| 4,114,090 | 9/1978 | Poskitt | 324/61 QS |
| 4,588,943 | 5/1986 | Hirth | 324/61 P |
| 4,711,244 | 12/1987 | Kuzara | 128/632 |

FOREIGN PATENT DOCUMENTS 2912349 10/1980 Fed. Rep. of Germany ...... 128/734
2919230 11/1980 Fed. Rep. of Germany ... 324/61 QS Primary Examiner—Lee S. Cohen

[57] ABSTRACT

Portable, battery-powered apparatus for monitoring a parameter of human skin includes probe structure with a probe member that has a pair of spaced electrodes for engagement with a skin surface to be monitored. A switch responsive to engagement of the probe member with a skin surface to be monitored provides an output signal. Monitoring circuitry includes pulse generator circuitry coupled to the electrodes and adapted to apply output pulses at a rate that is a function of the capacitance of the skin surface engaged by the electrodes to gate circuitry. Timer circuitry responsive to the output signal of the switch conditions the gate circuitry to pass pulse signals from the pulse generator circuitry to counter circuitry for accumulation. A display of the accumulated count provides an indication of the moisture content of the skin surface contacted by the probe electrodes.

18 Claims, 2 Drawing Sheets

MONITORING APPARATUS

This invention relates to monitoring apparatus, and more particularly to apparatus for evaluating moisture content of human skin.

The upper layers of human skin (the stratum corneum) play a major role in maintaining the water balance of the tissue necessary for a healthy, soft and smooth skin. Under a number of normal environmental conditions, however, water loss can increase, leading to skin dryness that is manifested by rough appearance of the skin and the skin's susceptibility to trauma from otherwise inconsequential physical insult. As low relative humidity in the environment causes water to escape the skin at a higher rate, a significant segment of the population who work and live in environments where low relative humidity conditions exist suffer from dry skin.

Instruments for assessing the relative condition of the skin by sensing water in tissue can provide information on relative condition of the skin. Such instruments can also be used to evaluate the relative efficiency of moisturizers, for example. A number of systems have been proposed to monitor parameters which change as the water content of the skin changes. Although much of such proposed instrumentation is costly and complex, some, such as ohmmeters which measure the electrical resistance of the skin, are relatively inexpensive and simple to operate. Such ohmmeter-type systems have a number of disadvantages, however, including variations in interelectrode distance between measuring and reference electrodes; the pressure with which the electrodes contact the skin; and skin residues such as cosmetics or skin oil which can influence the electrical resistance.

In accordance with the invention, there is provided apparatus for monitoring a parameter of human skin that includes probe structure including a probe member that has a pair of spaced electrodes for engagement with a skin surface to be monitored. Switch means responsive to engagement of the probe member with a skin surface to be monitored provides an output signal. Monitoring circuitry includes gate circuitry, pulse generator circuitry coupled to the electrodes and adapted to apply output pulses at a rate that is a function of the capacitance of the skin surface engaged by the electrodes to the gate circuitry, counter circuitry coupled to the output of the gate circuitry, timer circuitry responsive to the output signal of the switch means for applying a conditioning signal to the gate circuitry so that the conditioned gate circuitry passes pulse signals from the pulse generator circuitry to the counter circuitry for accumulation, and output means responsive to the counter circuitry for providing an indication of a parameter of the skin surface contacted by the probe electrodes.

In preferred embodiments, the apparatus is compact and portable, the monitoring circuitry is battery powered, and the output means includes a plural order decimal display that indicates the relative condition of the skin being monitored.

In a particular embodiment, the pair of electrodes includes an annular ground electrode and a signal electrode disposed within the annular ground electrode on an end surface of the probe member, the probe member is mounted on housing structure for reciprocating movement towards and away from the switch means, biasing means coupled to the probe member urges the probe member away from the switch means, and a switch actuator member carried by the probe member is adjustable to vary the spacing between the switch actuator member and the switch means. The pulse generator circuitry is of the RC oscillator-type and has an output pulse rate in excess of one kilohertz that varies in response to changes in electrode capacitance, and the timer circuitry applies the conditioning signal to the gate circuitry for a time duration of less than one second, the resulting number of pulses accumulated by the counter circuitry during that predetermined time interval providing an indication of the moisture content of the skin surface being monitored. The monitoring further includes means to adjust the time duration of the conditioning signal, means to adjust the output pulse rate of the pulse generator circuitry, and test signal means for applying a calibration check signal to the monitoring circuitry.

Other features and advantages of the invention will be seen as the following description of a particular embodiment progresses, in conjunction with the drawings, in which.

DESCRIPTION OF PARTICULAR EMBODIMENT

Figure 1:
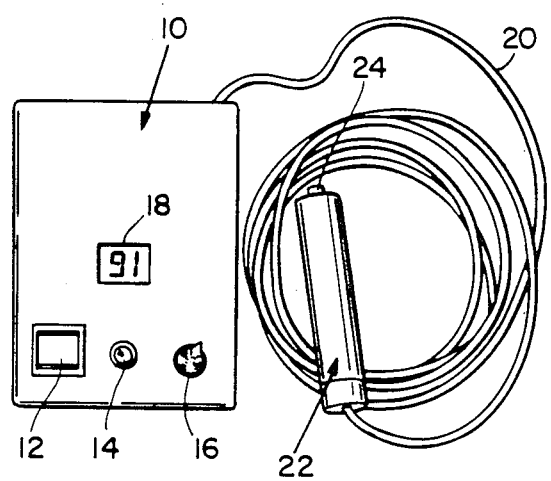
FIG. 1 is a perspective view of monitoring apparatus in accordance with the invention.
Figure 2:
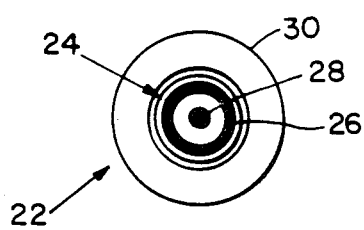
FIG. 2 is an end view of the probe employed in the monitoring apparatus of FIG. 1.

Shown in FIG. 1 is a monitoring system that includes control unit 10 with on/off switch 12, calibration check button 14, calibration adjust control 16 and two-order decimal display 18 of moisture index. Cable 20 connects housing 10 to probe unit 22 that has a diameter of about 2¼ centimeters and a length of about eleven centimeters. Probe member 24 that protrudes from one end of unit 22 has a diameter of about one centimeter and carries annular ground electrode 26 and center electrode 28, as indicated in FIG. 2.

Figure 3:
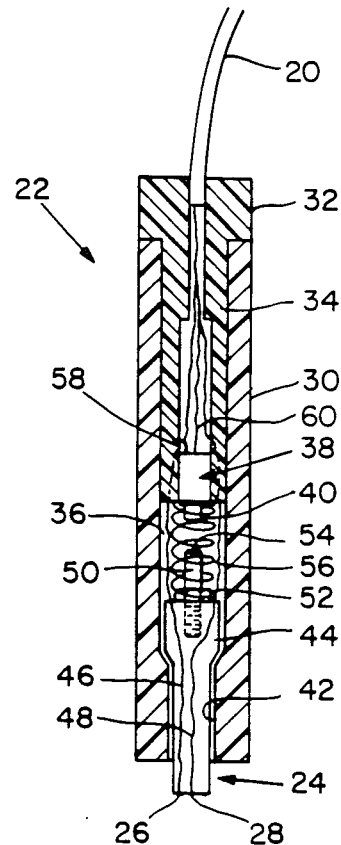
FIG. 3 is a sectional view of the probe employed in the monitoring apparatus of FIG. 1.

Further details of the probe unit may be seen with reference to FIG. 3. Probe unit 22 includes cylindrical body 30 of polymeric material, and cap member 32 which has projection 34 extends into cylindrical cavity 36 of body 30. Supported on projection 34 is switch unit 38 that has projecting actuator 40. Probe member 24 is guided for reciprocating movement in body channel 42 and has a body portion 44 of enlarged diameter. Electrical conductor wires 46, 48 extend from electrodes 26, 28 through probe member 24 and cavity 36 to cable 20 that extends through cap 32. Also threadedly carried by probe member 24 is rod member 50. Nut 52 permits adjustment of the spacing of rod head 54 from switch actuator 40. Spring 56 biases probe member 24 to its forward position with its end portion projecting about one half centimeter from the end of probe housing 30. Switch 38 has ground conductor 58 connected to conductor 46 and signal conductor 60 that is disposed in cable 20 together with conductors 46, 48.

Figure 4:
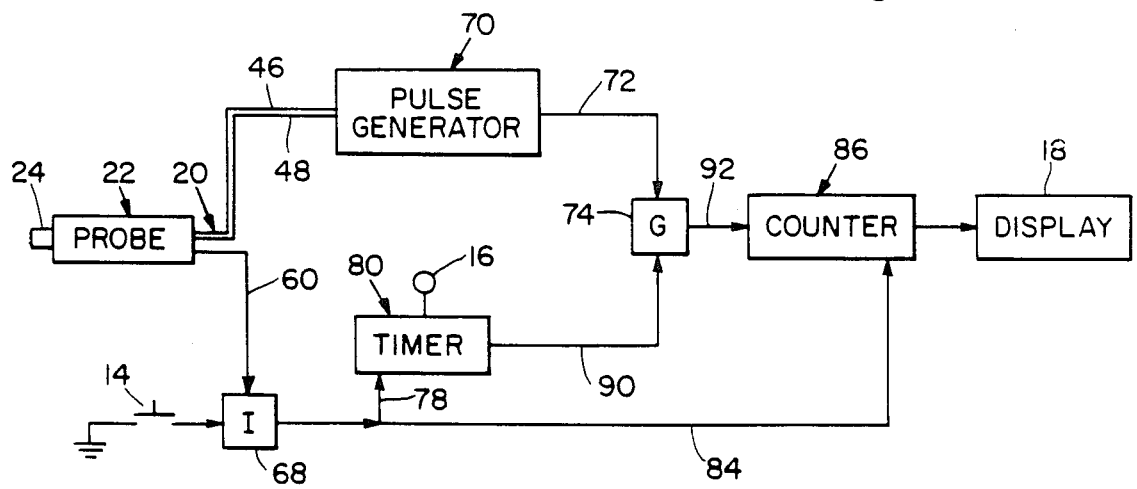
FIG. 4 is a block diagram of circuitry employed in the monitoring apparatus shown in FIG. 1.
Figure 5:
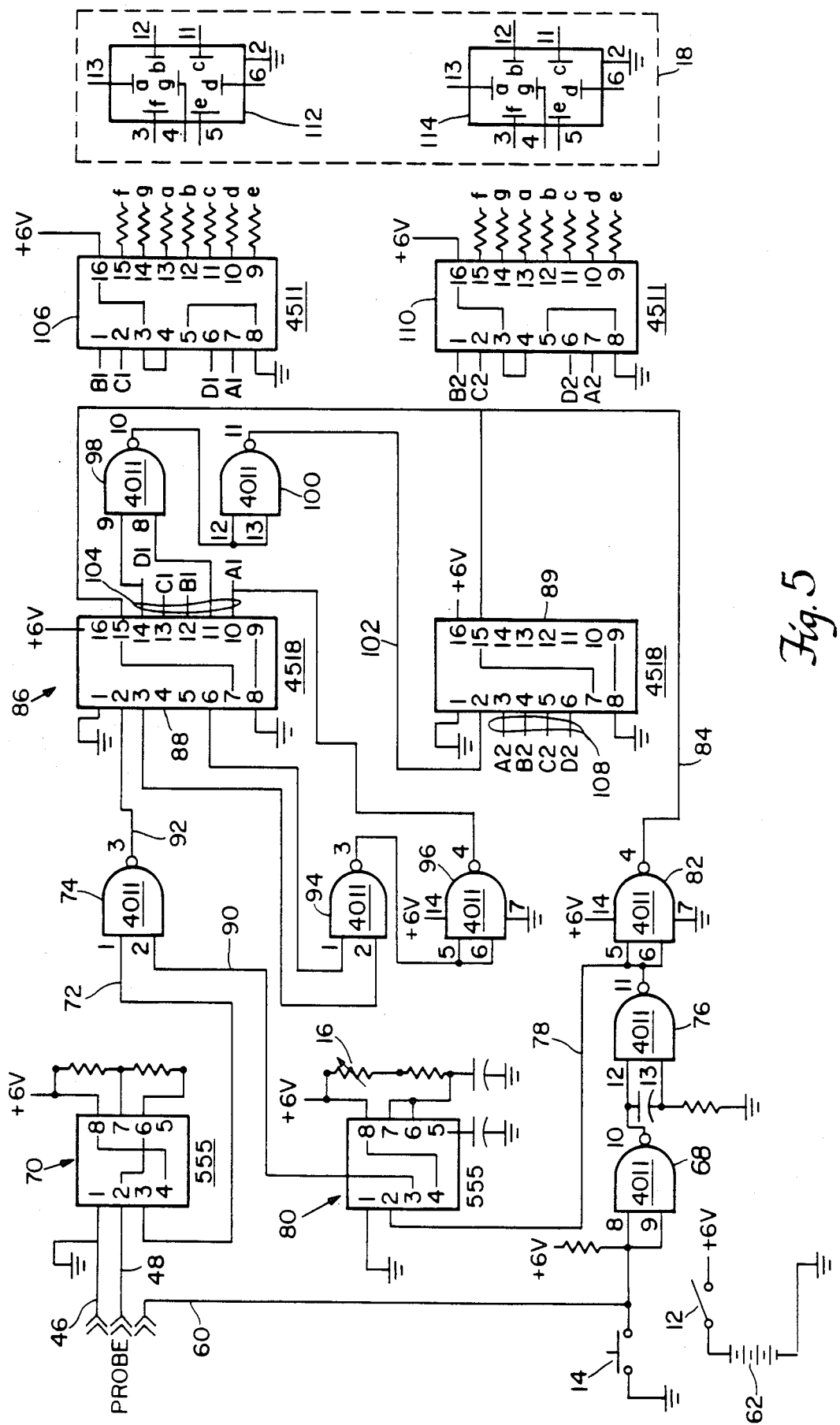
FIG. 5 is a schematic diagram of the monitoring circuitry of FIG. 4.

Aspects of circuitry in control unit 10 may be seen with reference to FIGS. 4 and 5. FIG. 4 is a block diagram of circuitry employed in the monitoring apparatus shown in FIG. 1, and FIG. 5 is a schematic diagram of the monitoring circuitry of FIG. 4. Switch 12 connects battery 62 in circuit. Input lines 46 and 48 are connected to oscillator-type pulse generator 70; and its output line 72 is connected to NAND circuit 74. Input line 60 is connected to inverter 68 and a signal from switch 38 supplied on line 60 is applied by inverter 68 to one shot circuit 76 that upon triggering, provides an output (of fifty microseconds duration) on line 78 to timer circuit 80. The output signal of circuit 76 is also applied through inverter 82 as a reset signal on line 84 to counter 86 (that has two units 88, 89, each of which provides outputs of two decimal orders and associated circuits 94, 96, 98, 100). In response to the trigger signal on line 78, timer 80 provides an output signal on line 90 to a second input of NAND circuit 74 to condition that NAND circuit to pass pulses from circuit 70 on line 92 to the first order input of counter unit 88. Circuits 94, 96 connect the first order stage of unit 88 to the second order stage, and circuits 98, 100 connect outputs of the second order stage of unit 88 over line 102 to the first order stage of unit 89. Outputs of the second order stage of counter unit 88 are applied over lines 104 to its driver stage 106 and output signals from the first order stage of counter unit 89 are similarly applied over lines 108 to its driver stage 110. Outputs from the driver stages 106, 110 are in turn applied to corresponding LED circuits 112, 114, respectively, in display 18. It will be apparent that other circuit and/or display arrangements, etc. may be utilized.

In use, the tip 24 of probe 22 is placed on the skin area whose moisture is to be measured, and pressure is applied to retract probe member 24 into the probe housing 30 against the biasing force of spring 56 sufficiently for actuator head 54 to operate switch 36 and apply a signal over line 60 to trigger one shot circuit 76. The resulting output of circuit 76 operates timer 80 and resets the counters 88, 89. Timer 80 produces an output on line 90 of duration as adjusted by resistor 16 to condition NAND circuit 74. The capacitance of the contacted portion of the skin across electrodes 26 and 28 is coupled over line 48 to oscillator 70 which produces output pulses at a frequency on the order of 25 kilohertz (the pulse rate being reduced as the sensed skin moisture increases) over line 72 to NAND circuit 74. During the time interval of the signal on line 90 (adjustable over range of about 10 to 40 milliseconds by control 16), NAND circuit 74 is conditioned and passes the oscillator pulses on line 72 over line 92 to step counter units 88, 89 to accumulate a count which is indicated as a two order decimal number on display 18, the lowest order of the accumulated pulse count being suppressed.

The invention provides a portable, battery powered instrument that is simple and reliable to use for monitoring a parameter of the skin to provide an indication of moisture content and skin quality as a function of capacitance.

While a particular embodiment of the invention has been shown and described, various modifications will be apparent to those skilled in the art, and therefore it is not intended that the invention be limited to the disclosed embodiment or to details thereof, and departures may be made therefrom within the spirit and scope of the invention.

What is claimed is:

1. Apparatus for monitoring a parameter of human skin comprising probe structure including a probe member, said probe member having a pair of spaced electrodes for engagement with a skin surface to be monitored, switch means responsive to engagement of said probe member with a skin surface to be monitored for providing an output signal, monitoring circuitry including gate circuitry, pulse generator circuitry coupled to said electrodes and said gate circuitry and adapted to apply output pulses at a rate that is a function of a parameter of the skin surface engaged by said electrodes to said gate circuitry, counter circuitry coupled to the output of said gate circuitry, timer circuitry coupled to said switch means and said gate circuitry and responsive to the output signal of said switch means for applying a conditioning signal for a predetermined period of time to said gate circuitry so that the conditioned gate circuitry passes pulse signals from said pulse generator circuitry to said counter circuitry for accumulation, and .

output means responsive to said counter circuitry for providing an indication of a parameter of the skin surface contacted by said probe electrodes.

2. The apparatus of claim 1 wherein said probe structure further includes housing structure in which said switch means is mounted, said probe member being mounted on said housing structure for movement towards and away from said switch means.

3. The apparatus of claim 1 and further including biasing means coupled to said probe member for urging said probe member away from said switch means.

4. The apparatus of claim 3 wherein said probe structure includes a switch actuator member, and further including means to adjust the spacing of said switch actuator member and said switch means.

5. The apparatus of claim 1 wherein said pair of electrodes includes an annular ground electrode and a signal electrode disposed within said annular ground electrode, said annular and signal electrodes being disposed for concurrent engagement with the skin surface to be monitored.

6. The apparatus of claim 1 wherein said pulse generator circuitry is of the RC oscillator-type and the output pulse rate of said pulse generator circuitry is in excess of one kilohertz.

7. The apparatus of claim 1 wherein said timer circuitry includes means for applying said conditioning signal to said gate circuitry for a time duration of less than one second.

8. The apparatus of claim 1 wherein said output means includes a plural order digital display.

9. The apparatus of claim 1 wherein said monitoring circuitry is battery powdered.

10. The apparatus of claim 1 wherein said pair of electrodes includes an annular ground electrode and a signal electrode disposed within said annular ground electrode, said annular and signal electrodes being disposed for concurrent engagement with the skin surface to be monitored and said probe structure further includes housing structure in which said switch means is mounted, said probe member being mounted on said housing structure for reciprocating movement towards and away from said switch means, and biasing means coupled to said probe member urges said probe member away from said switch means.

11. The apparatus of claim 10 wherein said probe structure includes a switch actuator member carried by said probe member, and further including means to adjust the spacing of said switch actuator member and said switch means.

12. Apparatus for monitoring a parameter of human skin comprising probe structure including a probe member, said probe member having a pair of spaced electrodes for engagement with a skin surface to be monitored, switch means carried by said probe structure and responsive to engagement of said probe member with a skin surface to be monitored for providing an output signal, monitoring circuitry including gate circuitry, pulse generator circuitry of the RC oscillator-type coupled to said electrodes and said gate circuitry and adapted to apply output pulses to said gate circuitry at a rate that is in excess of one kilohertz and is variable as a function of the capacitance of the skin surface engaged by said electrodes, counter circuitry coupled to the output of said gate circuitry, timer circuitry coupled to said switch means and said gate circuitry and responsive to the output signal of said switch means for applying a conditioning signal to said gate circuitry for a predetermined period of time of less than one second duration, so that the conditioned gate circuitry passes pulse signals from said pulse generator circuitry to said counter circuitry for said predetermined period of time for accumulation, and output means responsive to said counter circuitry for providing an indication of the capacitance of the skin surface contacted by said probe electrodes.

13. The apparatus of claim 12 and further including means to adjust the time duration of said conditioning signal, means to adjust the output pulse rate of said pulse generator circuitry, and test signal means for applying a calibration check signal to said monitoring circuitry.

14. The apparatus of claim 12 wherein said apparatus is portable and said monitoring circuitry is battery powered.

15. Portable, battery-powered apparatus for monitoring a parameter of human skin comprising probe structure including housing structure and a probe member, said probe member having a an annular ground electrode and a signal electrode disposed within said annular ground electrode on a generally planar and end surface of said probe member, said annular and signal electrodes being disposed for concurrent engagement with the skin surface to be monitored, switch means mounted in said housing structure, said probe member being mounted on said housing structure for reciprocating movement towards and away from said switch means, biasing means coupled to said probe member for urging said probe member away from said switch means, said switch means being responsive to engagement of said probe member with a skin surface to be monitored for providing an output signal, monitoring circuitry including gate circuitry, pulse generator circuitry coupled to said electrodes and said gate circuitry and adapted to apply output pulses to said gate circuitry at a rate that is a function of a parameter of the skin surface engaged by said electrodes, counter circuitry coupled to the output of said gate circuitry, timer circuitry coupled to said switch means and said gate circuitry and responsive to the output signal of said switch means for applying a conditioning signal for a predetermined period of time so that the conditioned gate circuitry passes pulse signals from said pulse generator circuitry to said counter circuitry for accumulation, and output means responsive to said counter circuitry for providing an indication of a parameter of the skin surface contacted by said probe electrodes.

16. The apparatus of claim 15 wherein said probe structure includes a switch actuator member carried by said probe member, and further including means to adjust the spacing of said switch actuator member and said switch means.

17. The apparatus of claim 16 and further including means to adjust the time duration of said conditioning signal, and test signal means for applying a calibration check signal to said monitoring circuitry.

18. The apparatus of claim 17 wherein said output means includes a plural order digital display.

* * * * *